(12) United States Patent
Kannan et al.

(10) Patent No.: US 6,555,682 B1
(45) Date of Patent: Apr. 29, 2003

(54) TWO-PHOTON RESPONSIVE CHROMOPHORES CONTAINING ELECTRON ACCEPTING CORES

(75) Inventors: Ramamurthi Kannan, Cincinnati, OH (US); Loon-Seng Tan, Centerville, OH (US); Richard A. Vaia, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 10/171,567

(22) Filed: Jun. 13, 2002

(51) Int. Cl.[7] ............... C07D 417/14; C07D 417/10; C07D 251/24
(52) U.S. Cl. ..................... 544/180; 544/215
(58) Field of Search ................. 544/180, 215

(56) References Cited

U.S. PATENT DOCUMENTS

| | | | |
|---|---|---|---|
| 5,770,737 A | 6/1998 | Reinhardt et al. | 546/285 |
| 5,859,251 A | 1/1999 | Reinhardt et al. | 546/255 |
| 6,100,405 A | 8/2000 | Reinhardt et al. | 548/250 |
| 6,300,502 B1 | 10/2001 | Kannan et al. | 548/150 |

*Primary Examiner*—John M. Ford
*Assistant Examiner*—Kahsay Habte
(74) *Attorney, Agent, or Firm*—Charles E. Bricker; Thomas L. Kundert

(57) ABSTRACT

Provided are chromophores of the formula

Q—(—L—Z)$_x$, wherein x is 3 or 4, wherein Q is selected from the group consisting of

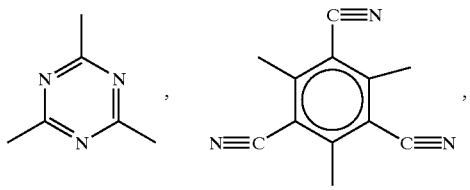

-continued

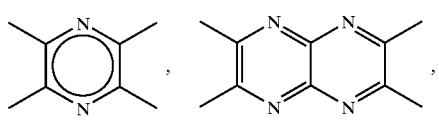

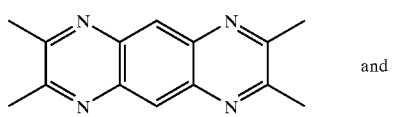

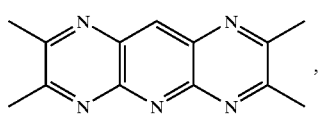

wherein L is selected from the group consisting of

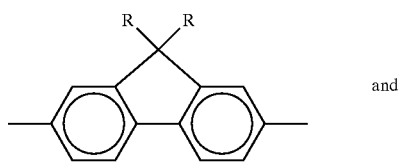

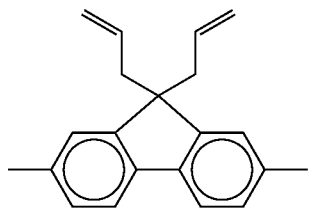

wherein R is an alkyl group having 1 to 20 carbon atoms, and wherein Z is selected from the group consisting of

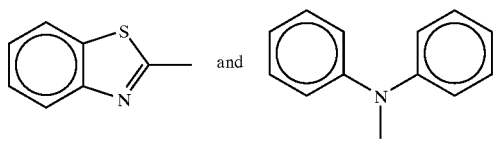

5 Claims, No Drawings

TWO-PHOTON RESPONSIVE CHROMOPHORES CONTAINING ELECTRON ACCEPTING CORES

RIGHTS OF THE GOVERNMENT

The invention described herein may be manufactured and used by or for the Government of the United States for all governmental purposes without the payment of any royalty.

BACKGROUND OF THE INVENTION

The present invention relates to chromophores with very large two-photon absorption cross-sections.

Two-photon or multiphoton absorption occurs through the simultaneous absorption of two or more photons via virtual states in an absorbing medium, with the former being more common. For a given chromophore, these absorption processes take place at wavelengths much longer than the cut-off wavelength of its linear (single-photon) absorption. In the case of two-photon absorption (TPA), two quanta of photons may be absorbed from a single light source (degenerate TPA) or two sources of different wavelengths (non-degenerate TPA). Although multiphoton absorption processes have been known since 1931, this field remained dormant largely due to the lack of TPA-active materials with sufficiently large cross-sections. In the mid-1990s, several new classes of chromophores exhibiting very large effective TPA cross-section ($\sigma_2'$) values were reported. In conjunction with the increased availability of ultrafast high-intensity lasers, the renewed interest has not only sparked a flurry of activities in the preparation of novel dye molecules with enhanced $\sigma_2'$ values, but also many previously conceived applications based on TPA process in photonics and biophotonics are now enabled by these new chromophores. It is important to recognize the following features of two-photon materials technology: (a) upconverted emission, whereby an incident light at lower frequency (energy) can be converted to an output light at higher frequency, for instance, IR to UV-Vis upconversion; (b) deeper penetration of incident light; (c) highly localized excitation allowing precision control of in-situ photochemical events in the absorbing medium, thereby minimizing undesirable activities such as photodegradation or photobleaching; (d) fluorescence when properly manipulated allows information feedback. It is anticipated that further ingenious utilization of these basic characteristics will lead to practical applications other than those already emerged in such diverse areas as fluorescence imaging, data storage, eye and sensor protection, microfabrication of microelectromechanical systems (MEMS), photodynamic therapy, etc.

In U.S. Pat. No. 5,770,737, Reinhardt et al disclose asymmetrical dyes with large two-photon absorption cross-sections and in U.S. Pat. No. 5,859,251, Reinhardt et al disclose symmetrical dyes with large two-photon absorption cross-sections. The asymmetrical dyes have the structure Acceptor-Core-Donor, and the symmetrical dyes have the structures Acceptor-Core-Acceptor and Donor-Core-Donor. In U.S. Pat. No. 6,300,502, Kannan et al disclose multi-branched TPA chromophores with 4, 5 or 6 branches from the core, thereby increasing the number density, i.e., the number of TPA-active subunits within the individual chromophore molecules.

Accordingly, it is an object of the present invention to provide new multi-branched TPA chromophores.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there are provided novel TPA chromophores having the structure

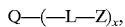

wherein x is 3 or 4, wherein Q is selected from the group consisting of

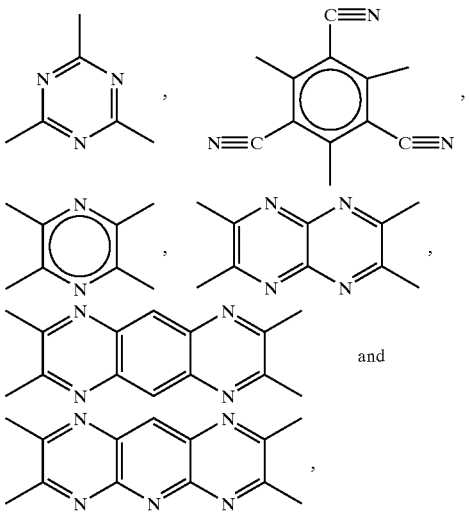

wherein L is selected from the group consisting of

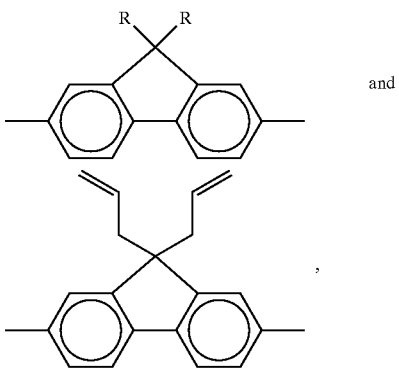

wherein R is an alkyl group having 1 to 20 carbon atoms, and wherein Z is selected from the group consisting of

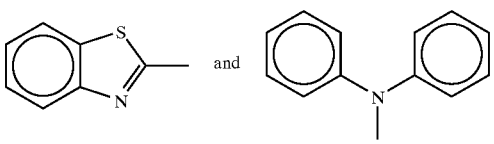

The chromophores of this invention can be synthesized following the procedures given in the following Examples which illustrate the invention:

EXAMPLE 1

2-Bromofluorene

To a solution of fluorene (16.6 g, 0.1 mol), in propylene carbonate (125 mL), at 60° C., N-bromo succinimide (17.8 g, 0.1 mol) was added in one portion, and the mixture was allowed to cool over a period of 1 hour. The solids separated on dilution with water (2 L), were collected, dissolved in toluene (250 mL), and the toluene solution was washed with water. The solids left after concentration were recrystallized from ethanol-water, 23.3 g (95% yield), m.p. 95.6–101.3° C. Mass Spec: m/z 322, 324, 326 (M$^+$ dibromo), 244,246 (M$^+$).

EXAMPLE 2

2- Bromo-7- iodofluorene

A mixture of 2-bromofluorene (12.61 g, 50 mmol), acetic acid (125 mL), water (9 mL), concentrated sulfuric-acid (4 mL), iodine (5.1 g, 20.1 mmol) and iodic acid (2.2 g, 12.5 mmol) was heated at 80–90° C. for 2 hours, cooled and filtered. The solids were washed with acetic acid (100 mL) and water (500 mL), to yield the product 14.7 g (79% yield), m.p. 179–185° C. Mass Spec: m/z 418 (M$^+$ diiodo), 370, 372 (M$^+$ iodobromo), 322, 324,326 (M$^+$ dibromo).

EXAMPLE 3

2-Bromo-7-iodo-9,9-didecylfluorene

To a mechanically stirred mixture of 7-iodo-2-bromofluorene (from example 2; 41.34 g, 0.1114 mol), DMSO (100 mL), potassium iodide (1.7 g), and powdered potassium hydroxide (28 g) cooled in a cold water bath, 1-bromodecane (53 mL) was added dropwise, and the mixture was stirred for 24 hours. The oil that separated on dilution with water, was extracted with toluene. Toluene extract was washed with water, dried and concentrated. The residual oil was passed through a column of 300 g alumina. Elution with 900 mL hexanes gave the product as an oil, 65 g This was left in 200 mL of isopropanol, when the product solidified, 58.63 g (81% yield), m.p. 43–45° C. Mass Spec.: m/z 698 (M$^+$ diiodo), 650,652 (M$^+$).

EXAMPLE 4

(7-Bromo-9,9-didecyl-fluoren-2-yl)diphenylamine

A mixture of 2-bromo-7-iodo-9,9-didecylfluorene (52.13 g, 0.08 mol), diphenylamine (15.6 g, 0.0922 mol, 1.152 eq), potassium carbonate (25.5 g, 0.1844 mol), tris(2-(2-methoxyethoxy)ethyl)amine (TDA-1, 5 mL), copper bronze (3.0 g, 0.05 g atom) and xylenes (75 mL) was brought to reflux, and 35 mL, of xylenes were distilled off to reach a reaction temperature of 160° C. The reaction was maintained at this temperature for 18 hours. Some more solvent was distilled off to reach a reaction temperature of 175° C., where the reaction was held for additional 6 hours. The mixture was then cooled, diluted with 100 mL toluene, filtered, the filtrate was concentrated, and the residue was transferred to a column of 600 g of silica gel. Elution with 750 mL hexanes returned a mixture of dibromo and bromoiodo fluorenes as an oil, 10.3 g Elution with heptane-toluene, 1:1, gave the product, 33.48 g (61 % yield, 77% yield on consumed bromoiodo fluorene), m.p. 66.8–69.2° C. Mass Spec: 691, 693 (M$^+$).

EXAMPLE 5

2,4,6-trist[7-(Diphenylamino)-9,9-didecylfluoren-2-yl]-1,3,5-triazine (AF-450)

To a solution of (7-bromo-9,9-didecyl-fluoren-2 -yl) diphenylamine (12.46 g, 18 mmol), in THF (75 mL) cooled in a dry-ice acetone bath, n-butyl lithium (1.6 M solution in hexanes, 12 mL, 19.2 mmol, 1.07 equivalents) was syringed in. After 25 minutes, a solution of cyanuric fluoride (0.81 g, 6 mmol) in THF (3 mL) was added, when the temperature rose to −50° C. The mixture was left in the cooling bath, was allowed to come to room temperature overnight, and then diluted with water and toluene. The organic phase was dried over magnesium sulfate, concentrated and eluted out with 10% toluene-heptane as a glassy material. The product solidified on standing in isopropanol, 6.55 g, (57% yield); m.p.121–122° C. LRFAB Mass Spec:1917.4, 1916.41 and 1915.4 amu (M$^+$+1). Anal. Calcd. for $C_{138}H_{174}N_6$: C, 86.47%; H, 9.15%; N, 4.38%. Found: C, 86.49%; H, 9.05%; N, 4.35%.

EXAMPLE 6

2,7 Dibromo-9,9-diprop-2-enylfluorene

To a mixture of 2,7-dibromofluorene (16.2 g, 50 mmol), potassium hydroxide (16.8 g, 300 mmol), potassium iodide (1.08 g, 6.5 m. mol) and DMSO (45 mL), cooled in an ice-water bath, allyl bromide (11 mL, 127 mmol) was added dropwise, and the mixture was stirred at room temperature for 18 hours. The solids that separated on dilution with water were collected, and recrystallized from heptane and once from methanol, 13.2 g. (64 % yield), m.p. 149–150° C. Mass Spec: m/z 402, 404,406 (M$^+$). Anal. Calcd. for $C_{19}H_{16}Br_2$: C, 56.47%; H, 3.99%; Br, 39.54%. Found: C, 56.40%; H, 3.81 %; Br, 39.42%.

EXAMPLE 7

(7-Bromo-9,9-diprop-2-enylfluoren-2-yl) diphenylamine

A mixture of 2,7 dibromo-9,9-diprop-2-enylfluorene (40.4 g, 0.1 mol), diphenylamine (8.5 g, 0.05 mol), bis (dibenzylideneacetone)palladium(0) (0.3 g, 0.522 mmol), bis(diphenylphosphino)ferrocene (0.32 g, 0.57 mmol) sodium t-butoxide (5.6 g, 0.058 mol) and toluene (350 mL) was heated at 93° C. for 18 hours under nitrogen, and cooled. The mixture was diluted with toluene and water, and the toluene phase was dried and concentrated. The residue was chromatographed over 850 g of alumina. Elution with heptane led to the recovery of unreacted dibromo-diallylfluorene, 13.38 g, 33%, m.p. 134–137° C. Elution with 10% toluene-heptane yielded the desired product, m.p. 151–153° C., 11.74 g, 48% yield. Two successive recrystallizations from hexanes did not raise the m.p., 150.4–152.8° C. Mass Spec: m/z 491,493 (M$^+$). IR (KBr): 3068, 2977,1639,1589,1489 cm$^{-1}$. Anal. Calcd. for $C_{31}H_{26}BrN$; C, 75.61%; H, 5.32%; N, 2.84%; Br, 16.23%. Found: C, 75.56%; H, 5.27%; N, 2.68%. (Br- 17.1%). This reaction also produced some 2,7-bis(diphenylamino)-9,9-diallylfluorene, 1.09 g, m.p. 179–183° C. Mass Spec: m/z 580 (M$^+$).

EXAMPLE 8

2-Bromo-7-iodo-9,9-diprop-2-enylfluorene and 2,7-diiodo-9,9-diprop-2-enylfluorene To a mixture of 2-bromo-7-iodofluorene (129.5 g, 0.25 mol), obtained by iodination of 2-bromofluorene (see example 2), potassium hydroxide (118.0 g, 2.1 mol), potassium iodide (7.0 g, 0.042 mol) and DMSO (500 mL), allyl bromide was added dropwise at 15–20° C., the mixture was stirred for 18 hours and poured into 4 liters of water. The separated solids were collected, washed with water and dried, 155.48 g, m.p. 146.7–150.5° C. This was heated to reflux in 500 mL ethanol for 2 hours, cooled, filtered and solids were washed with ethanol, 146.5 g, m.p. 149.4–151.8° C., 93% yield. A portion of the crude product was recrystallized twice from hexanes, m.p. 152.3–153.7° C. Mass Spec: m/z 498($M^+$, diiodo), 450,452 (($M^+$, desired bromo iodo), 402, 404, 406 ($M^+$ dibromo). Anal. Calcd. for $C_{19}H_{16}BrI$: C, 50.58%; H, 3.57%; Br, 17.71%; I, 28.13%. Found: C, 49.87%; H, 3.63%; Br, 14.10%; I, 32.26%.

EXAMPLE 9

2-Bromo-7-(diphenylamino)-9,9-diprop-2-enylfluorene

A mixture of 2-bromo-7-iodo-9,9-diprop-2-enylfluorene (major component) and 2,7-diiodo-9,9-diprop-2-enylfluorene (45.3 g, 0.1 mol), diphenylamine (17.0 g, 0.1 mol), potassium carbonate (30.38 g, 0.22 mol), copper bronze (4.8 g, 76 mmol), copper(I) iodide (1.0 g, 5.25 mmol), dichlorobenzene (85 mL) and toluene (50 mL), was heated to reflux, and toluene and water were distilled off to get a reaction temperature of 182–183° C. After 7 hours, the reaction was cooled, diluted with 100 mL methylene chloride and filtered. The salts were washed with 3×50 mL methylene chloride. The combined filtrate was concentrated and chromatographed over a column of alumina (800 g). Elution with 10% toluen-heptane gave the product, 27.21 g, 55% yield, m.p. 141.4–143.3° C. Mass Spec: m/z 539 ($M^+$, iodo analog), 491,493 ($M^+$, desired bromo). Anal. Calcd. for $C_{31}H_{26}BrN$: C, 75.61%; H, 5.32%; N, 2.84%; Br, 16.23%. Found: C, 74.02%; H, 5.37%; N, 2.68%; Br, 12.42%; I, 6.19%.

EXAMPLE 10

2,4,6-tris[(7-(Diphenylamino)-9,9-diprop-2-enylfluoren-2-yl]-1,3,5-triazine (AF-457)

To a solution of 2-bromo-7-(diphenylamino)-9,9-diprop-2-enylfluorene (22.16 g, 0.045 mol), in THF (200 mL), cooled in a dry ice-acetone bath, a solution of n-butyl lithium in hexanes (1.6M, 30 mL, 0.048 mol), was added by syringe over 5 minutes. After 25 minutes, over a 30 minute period, a solution of cyanuric fluoride (2.025 g, 0.015 mol), in THF (100 mL) was added to result in a greenish fluorescent solution, which turned orange at the end of additon. The mixture was allowed to warm up slowly to room temperature, diluted with toluene and water, and the organic phase was dried and concentrated. The residue was chromatographed over alumina (eluted with 1:3 toluene-heptane), rechromatographed over silica gel (eluted with 1:3 toluene-heptane), and then crystallized from 1:3 toluene-heptane. The desired product was obtained as a bright yellow solids, 11.84 g, 60% yield, m.p. 235–237° C. Recrystallization from 2:1 heptane-toluene raised its m.p. to 236–238° C. Mass Spec: m/z 1314 ($M^+$). Anal. Calcd. for $C_{96}H_{78}N_6$: C, 87.64%; H, 5.90%: N, 6.3%. Found: C, 87.59%; H, 6.06%; N, 6.15%.

EXAMPLE 11

Racemic Dihydrocitronellyl Bromide (1-bromo-3,7-dimethyloctane)

Concentrated sulfuric acid (17 mL) was added to 48% hydrobromic acid (100 mL) with stirring, and then 3,7-dimethyloctanol (dihydrocitronellol, Aldrich, 67 mL, 100 g) was added to the mixture. The mixture was then heated to 120–125° C., and kept at this temperature for 3 hours. The reaction was cooled, and extracted into heptane (300 mL). The heptane layer was washed with hydrochloric acid, water, sodium bicarbonate solution, dried and concentrated to leave an oil, 81.5 g. This oil was distilled under vacuum at a bath temperature of 120–125° C., to afford the bromide product as an oil, b.p. 85–87° C./10 mmHg, 78.2 g, 100% yield. Mass Spec: m/z 220,222 ($M^+$).

EXAMPLE 12

Racemeic and Meso 9,9-bis(3,7-Dimethyloctyl)-2,7-dibromofluorene

To a mechanically stirred mixture of 2,7-dibromofluorene (58.32 g, 0.18 mol), potassium iodide (3.0 g, 18 mmol), potassium hydroxide (50.4 g, 0.9 mol) and DMSO (150 mL), cooled in ice-water to 15° C., dihydrocitronellyl bromide (86.8 g, 0.392 mol) was added, and the mixture was stirred at room temperature for 18 hours. The mixture was poured into water, and the product was extracted into a mixture of 1:1 toluene-heptane. The organic phase was washed with water, dried and concentrated. The residual oil was refluxed with pyridine for 18 hours to quaternize any unreacted bromide, and the mixture was diluted with toluene-heptane, and the organic phase was washed with water, dried and concentrated. The residual orange oil was transferred to a column of 1050 g of alumina. Elution with hexanes (1800 mL) gave the product, 102.25 g, 94% yield, as a colorless oil. Mass Spec: m/z 602,604,606 ($M^+$). Anal. Calcd. for $C_{33}H_{48}Br_2$: C, 65.56%; H, 8.00%; Br, 26.44%. Found: C, 65.80%; H. 7.81%; Br, 26.30%.

EXAMPLE 13

Racemic and Meso [9,9-bis(3,7-Dimethyloctyl)-7-bromofluoren-2yl]diphenylamine

A mixture of 9,9-bis(3,7-dimethyloctyl)-2,7-dibromofluorene (56.2 g, 0.093 mol), diphenylamine (7.87 g, 0.0465 mol), bis(dibenzylideneacetone)palladium(0) (0.30 g, 0.52 mmol), bis(diphenylphosphino)ferrocene (0.32 g, 0.58 mmol), sodium t-butoxide (5.4 g, 0.0562 mol) and toluene (330 mL) was kept under nitrogen at 80° C. for 18 hours, and then at 100° C. for 5 hours. The mixture was cooled, diluted with toluene and water, and the organic phase was washed with water, dried and concentrated. The residual brown oil, 59 g, was transferred to a column of 600 g, silica gel. Elution with hexanes (1200 mL) led to the recovery of unreacted dibromofluorene, 28.09 g, mass spec, m/z 602, 604, 606. The desired product was eluted out with heptane as an oil, 28.49 g, 88.5% yield. Mass Spec: m/z 691,693 ($M^+$). Anal. Calcd. for $C_{45}H_{58}NBr$: C, 78.01 %; H, 8.44%; N, 2.02%; Br, 11.53%. Found: C, 77.62%; H, 8.46%; N, 1.88%; Br, 12.40%.

EXAMPLE 14

Diastereoisomeric Mixture of 2,4,6-tris [9,9-bis(3,7-Dimethyloctyl)-7-(diphenylamino)-fluoren-2yl]-1,3, 5 -triazine (AF-455)

To a solution of [9,9-bis(3,7-dimethyloctyl)-7-bromofluoren-2yl]diphenylamine (24.9 g, 36 mmol), in THF (150 mL), cooled in a dry ice-acetone bath, a solution of n-butyllithium in hexanes (1.6M, 24mL, 38.4 mmol) was added, and after 25 minutes, a solution of cyanuric fluoride (1.62 g, 12 mmol) in THF (100 mL). The mixture was allowed to warm up slowly to room temperature, and then diluted with toluene and water. The organic phase was washed with water, dried and concentrated. The residue was chromatographed over 700 g of alumina. The product was eluted with 10% toluene-heptane and isolated in two fractions, 4.7 g, and 7.05 g, as a yellow glassy material, 51% yield. HRMS M⁺ at 1917.31. Anal. Calcd. for $C_{138}H_{174}N_6$: C, 86.47%; H, 9.15%; N, 4.38%. Found: C, 86.66%; H, 9.20%; N, 4.25%.

The TPA values of the chromophores are shown Table 1. The chromophores AF-350 and AF-380 are included for comparison. AF-350 and AF-380 have the structure Q—(-L—Z)$_x$;

in AF-350, Q is N≡, L is

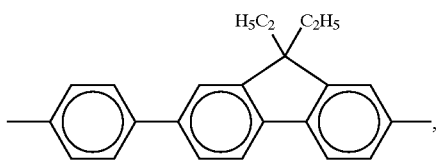

Z is

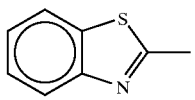

and x is 3;
and in AF-380, Q is N≡, L is

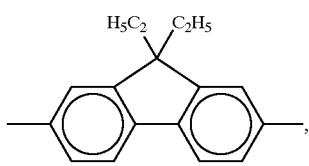

Z is

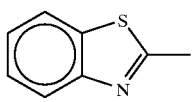

and x is 3.

TABLE 1

| Chromophore | $\lambda_{max}$ (nm) Linear Abs. | β cm/GW at 0.2 mol/L | $\sigma_2'$ (× 10⁻⁴⁸ cm⁴ · sec ph · molecule) | $\sigma_2'$/MW (× 10⁻⁵⁰ cm⁴ · sec · mole ph · molecule · g) |
|---|---|---|---|---|
| AF-350 | 392 | 13.5 | 250 | 19.2 |
| AF-380 | 428 | 12.0 | 270 | 25.1 |
| AF-450 | 415 | 20.0 | 395 | 20.6 |
| AF-455 | 410 | 12.3 | 333 | 17.4 |
| AF-457 | 414.5 | 13.5 | 278 | 21.1 |

Having thus described exemplary embodiments of the present invention, it should be noted by those skilled in the art that the disclosures herein are exemplary only and that alternatives, adaptations and modifications may be made within the scope of the present invention.

We claim:
1. A chromophore of the formula Q—(—L—Z)$_3$, wherein Q is

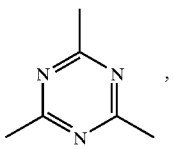

wherein L is selected from the group consisting of

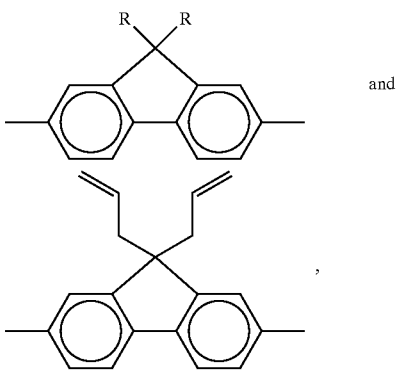

wherein R is an alkyl group having 1 to 20 carbon atoms, and wherein Z is selected from the group consisting of

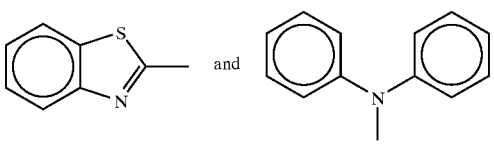

2. The chromophore of claim 1 wherein L is

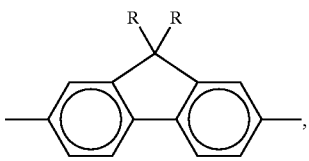

and Z is

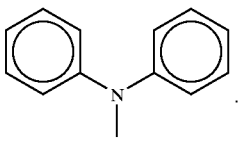

3. The chromophore of claim 2 wherein R is n-$C_{10}H_{21}$.

4. The chromophore of claim 2, wherein R is 3,7-dimethyloctyl.

5. The chromophore of claim 1, wherein L is 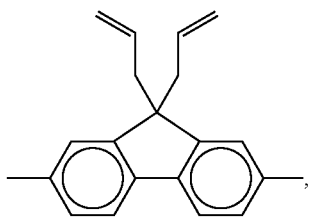 and Z is 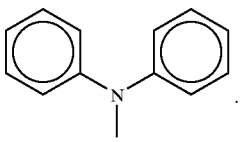.
* * * * *